United States Patent
Purcell

[11] Patent Number: 5,601,324
[45] Date of Patent: Feb. 11, 1997

[54] SAMPLE CONTAINER CLAMP

[76] Inventor: Kenneth S. Purcell, P.O. Box 1344, Greenwood, Nova Scotia, Canada, B0P 1N0

[21] Appl. No.: 566,963

[22] Filed: Dec. 4, 1995

[30] Foreign Application Priority Data

Jun. 14, 1995 [CA] Canada .................................. 2151783

[51] Int. Cl.⁶ .............................................. B25J 15/00
[52] U.S. Cl. ........................................ 294/31.2; 294/19.1
[58] Field of Search .............................. 294/1.4, 16, 19.1, 294/22, 27.1, 28, 31.1, 31.2, 33, 68.1, 68.3, 119.2, 165; 73/863, 864.51, 864.91; 220/752, 758, 759

[56] References Cited

U.S. PATENT DOCUMENTS

| | | | |
|---|---|---|---|
| 730,218 | 6/1903 | Anderson | 294/31.2 |
| 877,012 | 1/1908 | Sullivan | 294/16 |
| 1,965,638 | 7/1934 | Gerhardt | 294/19.1 X |
| 2,029,707 | 2/1936 | Dodelin . | |
| 2,994,551 | 8/1961 | Garnett | 294/15 |
| 3,679,253 | 7/1972 | Simms | 294/31.2 |
| 3,960,021 | 6/1976 | Jones | 294/19.1 X |
| 4,225,104 | 9/1980 | Larson | 294/19.1 X |
| 4,838,465 | 6/1989 | Metzger | 294/19.1 X |

FOREIGN PATENT DOCUMENTS

| | | |
|---|---|---|
| 677752 | 1/1964 | Canada . |
| 1267166 | 3/1990 | Canada . |

*Primary Examiner*—Johnny D. Cherry
*Attorney, Agent, or Firm*—Jones, Tullar & Cooper, P.C.

[57] ABSTRACT

This invention relates to a clamp used to securely hold a sample jar, bottle or container while it is manipulated by a handle to extract a sample from a host volume of liquid, such as water. The clamp provides first and second clamp members hinged together at one end, with one of the clamp members incorporating a length of friction material along the inner surface thereof. The clamp members may be locked together at the other ends thereof so as to clamp the container therebetween. One of the clamp members includes a hinged joint for a socket member, into which the end of an elongated handle can be threaded. The clamp is easy to use and inexpensive to manufacture, yet it provides improved security for the container and permits improved ease of manipulation when compared to prior art clamps.

14 Claims, 1 Drawing Sheet

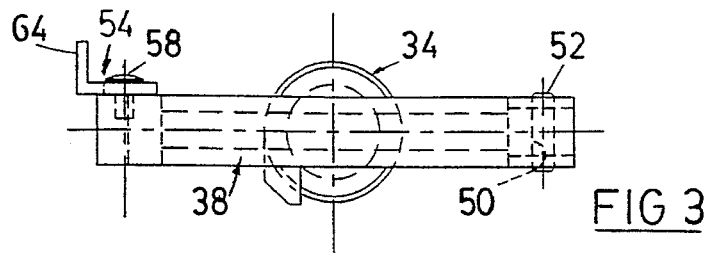
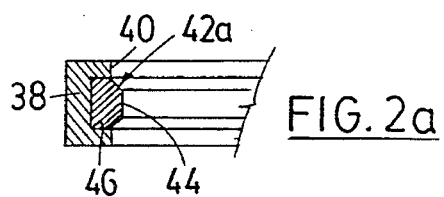
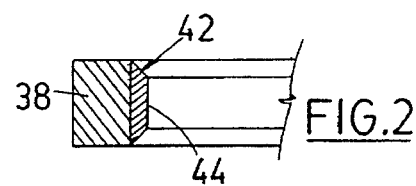
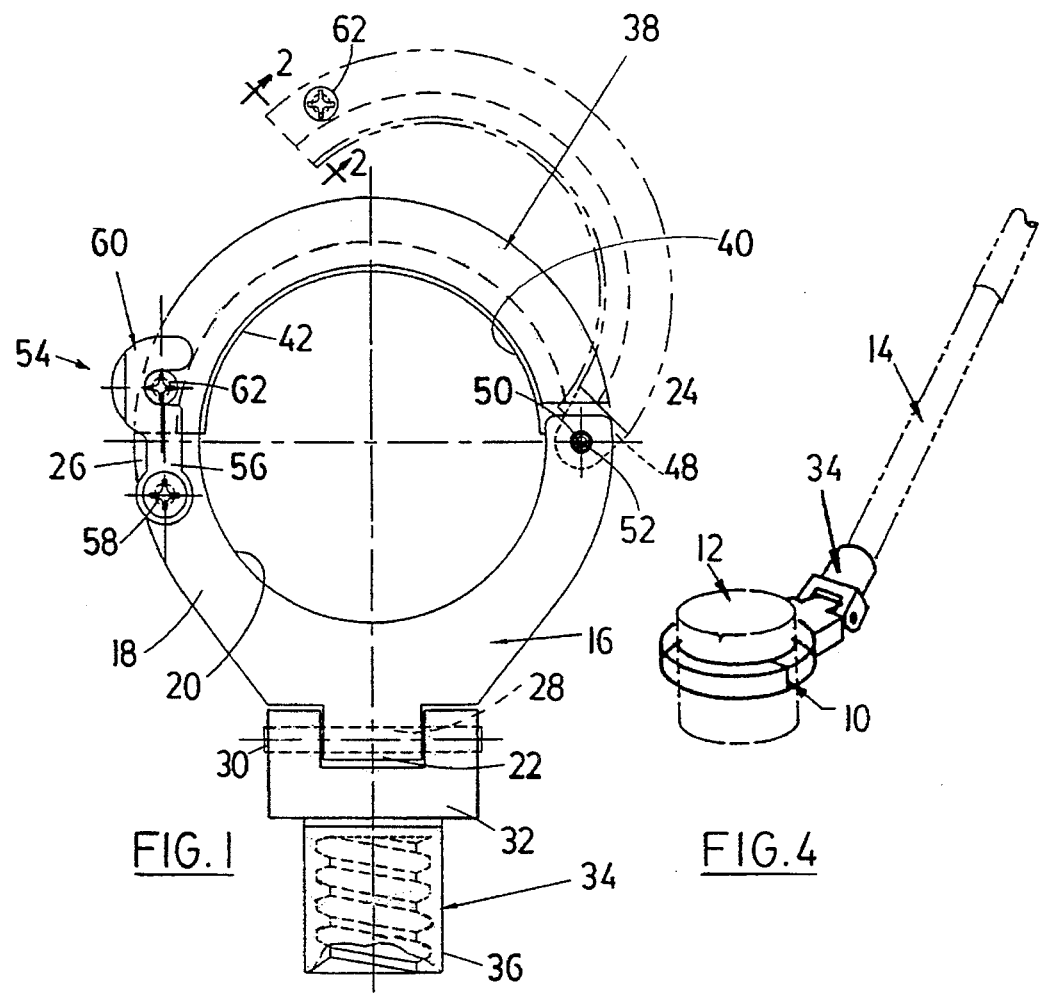

5,601,324

SAMPLE CONTAINER CLAMP

The present invention is related to the collection of water and other liquid samples in general and is particularly related to a clamp used to grip a sample collection jar or bottle.

BACKGROUND OF THE INVENTION

There are many instances in which it is necessary to collect samples of liquid for analysis purposes. Samples are taken regularly in accordance with Federal, Provincial or industrial monitoring programs from water treatment plants, waste-water treatment plants, P.O.L. compounds, collection systems, storm drains, manholes, catch basins, streams, rivers, reservoirs, water tables, run-offs, chemical plants and other facilities. Sample taking involves the introduction of a collection jar or other container into the liquid to be sampled and the subsequent removal of the container once a suitable volume of liquid has entered the container. It is important that the collection be made quickly and efficiently and that there be no spillage of liquid from the container as it is removed from the vat, stream, pond, or other main container holding the liquid of interest.

It is also important that the sample collected be an accurate representation of the liquid being sampled. In the past, cross contamination of samples has been a problem. Sterile stainless steel cylinders or glass bottles were connected to a pole and dipped into the sample. The sample volume was poured into collection jars or bottles and sent for analysis. To avoid cross contamination from sample to sample, a new stainless steel sterile cylinder or bottle was needed to collect samples from different locations. This meant that many bottles were required when many samples were to be taken.

Another problem associated with previous practices was the danger of manually dipping by hand into the host volume. Extra workers are required when retrieving samples from confined spaces. For example, if a manhole had to be monitored, it was necessary to use three people and considerable equipment for the set-up and sample taking. The person taking the sample would wear a safety harness while the others would set up safety triangles, gas monitoring equipment and a tripod. The person wearing the safety harness would connect to the tripod and lower himself into the manhole to take the samples. After the samples were taken, he would come up and the others would take down the equipment and move to the next sample point. This is a very costly exercise and can be dangerous for the workers involved.

SUMMARY OF THE INVENTION

The present invention overcomes the problems associated with prior art jar or bottle clamps, by providing a clamp that is readily secured to a collection jar to clamp the jar in such a manner that it will not be adversely harmed by the clamp. The clamp of the present invention also allows for the connection thereof to the threaded end of an elongated handle member such as a telescopic pole with a standard broom handle thread. Furthermore, the clamp of this invention permits articulation between the handle and the clamp itself so as to improve the ease of manipulation while a sample is being taken and while the full jar is removed from the host volume. The problems of cross contamination are avoided with this invention and the worker need not be concerned about dipping his hand into the host volume or coming particularly close to that volume while taking the sample. There is no more need for the extra personnel formerly required for taking samples from a confined space or the icy edge of a body of water in fall, winter, or spring.

Generally speaking, therefore the present invention may be considered as providing a clamp for secure attachment to a container, comprising: a first clamp member having an inner surface complementary to a wall portion of the container; a second clamp member having an inner surface complementary to another wall portion of the container; means hingedly connecting the second clamp member at one end thereof to an end of the first clamp member; means for locking the other end of the second clamp member to the other end of the first clamp member; friction means lining the arcuate surface of one of the clamp members; and handle attachment means hingedly connected to one of the clamp members intermediate the ends thereof.

BRIEF DESCRIPTION OF THE DRAWINGS

FIG. 1 is a plan view of the clamp of this invention shown in a locked condition, with the second clamp member being shown in an unlocked condition in dashed lines.

FIG. 2 is a cross section through the second clamp member taken on the line 2—2 of FIG. 1.

FIG. 2a is similar to FIG. 2 but shows an alternative cross section.

FIG. 3 is an end view of the clamp of the present invention.

FIG. 4 is a perspective view of the clamp of this invention in use, assembled to a collection container.

DESCRIPTION OF THE PREFERRED EMBODIMENT

With initial reference to FIG. 4 it will be seen that the clamp 10 of the present invention is used to hold a cylindrical jar, bottle or other container 12. The clamp 10 is to be manipulated by an elongated handle member 14 so that the container 12 can be introduced into a host volume of liquid, such as water, and then extracted from the host volume once a desired sample volume has been collected in the container.

Turning now to the other figures, the preferred embodiment of the present invention comprises a first clamp member 16 which is generally C-shaped, having an arcuate body 18 defining an arcuate inner surface 20 and a generally rectangular lug 22 extending from the body 18 intermediate the ends 24, 26 of the body 18. The lug 22 has a transverse bore 28 therethrough to receive a roll pin 30 that frictionally connects the yoke 32 of a handle socket member 34 to the body 18. The socket member 34 includes an internally threaded socket portion 36 that is adapted to threadedly receive the externally threaded end of the handle member 14. The handle member 14 could be a commercially available broom handle although it is preferred that the handle member be of the telescopic variety for most efficient operation during sampling.

A second, generally C-shaped clamp member 38 also has an arcuate inner surface 40, of essentially the same diameter as the inner surface 20 of the first clamp member. The second clamp member includes an arcuate friction element 42 that is adhered to and projects radially inwardly of the inner surface 40. The friction element 42 could be a rubber extrusion or it could be made from a plastics material. The material, like that of the clamp members and the socket member, should be such that it will not be affected deleteriously by the liquid to be sampled. Preferably, the friction element is shaped so as to have a radially innermost edge 44 that is of lesser depth or thickness than the portion that is adhered to the surface 40.

An alternative construction is shown in FIG. 2a, wherein the surface 40 is provided with an undercut recess 46, which recess is adapted to receive a friction element 42a in the form of an insert. The element 42a is otherwise the same as and performs the same functions as the element 42.

At one end the second clamp member is provided with a projecting lug 48 that fits within a slot at one end of the first clamp member. The lug 48 and the one end of the first clamp member are provided with a through bore 50 that receives a pin 52 so as to hingedly connect the second clamp member to the first clamp member. As can be seen in phantom lines in FIG. 1 the second clamp member can swing away from the first clamp member to allow the securement of the clamp 10 to the container 12.

At the other end thereof each of the clamping members is provided with locking means 54 that serve to lock the clamp members together and thereby hold a container 12 within the clamp 10. The locking means 54 includes a latch 56 hingedly attached to the first clamp member by a pin 58, the latch 56 including a C-shaped portion 60 at the end opposite the pin 58. An upstanding pin 62 on the second clamp member is located such that the C-shaped end of the latch 56 can engage it in a frictional manner and bias the two adjacent ends of the clamp members together in a clamping action. The latch 56 may include an upstanding lug 64 which can be grasped by the fingers or pushed by the thumb to facilitate pivoting movement of the latch between latched and unlatched conditions.

As can be seen, the clamp of the present invention is simple and economical to produce and it is effective in securely holding a cylindrical container within the confines of the two clamp members thereof. In use, the latch 56 is disengaged from the pin 62 and the second clamp member 38 is swung outwardly as shown in phantom lines in FIG. 1. The container 12 is introduced into the clamp and the second clamp member is swung back so that the latch 56 can be re-engaged with the pin 62. The friction element 42 or 42a helps to bias the container towards the first clamp member and it also helps to tension the locking means 54 to prevent inadvertent unlatching of the clamp members during use. The threaded end of the handle member 14 is threaded into the socket portion 36 and then the container 12 can be dipped into the host volume under the control of the handle member 14.

Because the socket portion 36 is connected to the first clamp member by a roll pin 30, there will be a fair bit of friction between the first clamp member and the socket portion. It is possible to preset the relative orientation between the handle and the clamp so that samples can be taken at any desired attitude. For extracting a sample from a manhole the clamp would be oriented at about 90° to the handle for vertical extraction whereas the clamp and handle would be set closer to an in-line orientation for extraction from a river, lake or pond.

Although the present invention has been described with respect to a cylindrical collection bottle, it is clear that the inventive aspects of the invention could be applied to other types of clamps, including clamps that could be adapted to hold containers or articles of different shapes and sizes. When doing so, the first clamp member would be shaped so as to be complementary to a first wall portion of the container and the second clamp member would be shaped so as to be complementary to another wall portion of the container. Also, the friction element 42, 42a could be provided on the first clamp member or the socket member 34 could be provided on the second clamp member. It is expected that a skilled artisan could modify the present invention so as to obtain the benefits thereof, but without departing from the spirit of the invention. Accordingly, the protection to be afforded this invention is to be determined from the claims appended hereto.

I claim:

1. A clamp for a generally cylindrical container, comprising: a first clamp member having an arcuate inner surface; a second clamp member having an arcuate inner surface; means hingedly connecting the second clamp member at one end thereof to an adjacent end of said first clamp member; means for locking the other end of said second clamp member to the other end of said first clamp member; friction means in the form of an elongated strip of resilient material adhered to said arcuate inner surface of said second clamp member and having a thickness at said arcuate inner surface of said second clamp member that is greater than the thickness at a radially innermost edge thereof; and handle attachment means hingedly connected to said first clamp member intermediate the ends thereof.

2. The clamp of claim 1 wherein said connecting means comprises a projecting lug at said one end of said second clamp member, which fits within a slot at said adjacent end of said first clamp member, a bore extending through said lug and said adjacent end of said first clamp member, and a hinge pin received in said bore.

3. The clamp of claim 2 wherein said locking means comprises a latch hingedly connected to the other end of said first clamp member, a locking pin at the other end of said second clamp member, and a generally C-shaped portion at a free end of said latch for latching engagement with said locking pin.

4. The clamp of claim 3 wherein said handle attachment means includes a lug formed on said first clamp member intermediate the ends thereof, a bore extending through said last-mentioned lug, and a socket member having a yoke portion hingedly connected to said last-mentioned lug by a roll pin, said socket member also having an internally threaded socket portion for threaded reception therein of an externally threaded end of a handle member.

5. A clamp for a generally cylindrical container, comprising: a first clamp member having an arcuate inner surface; a second clamp member having an arcuate inner surface; means hingedly connecting the second clamp member at one end thereof to an adjacent end of said first clamp member; means for locking the other end of said second clamp member to the other end of said first clamp member; an undercut recess in the inner surface of said second clamp member; friction means in the form of an insert held in said recess and projecting radially inwardly of said inner surface of said second clamp member along the length thereof; and handle attachment means hingedly connected to said first clamp member intermediate the ends thereof.

6. The clamp of claim 5 wherein said insert is an elongated strip of resilient material having a thickness within said recess greater than the thickness at a radially innermost edge thereof.

7. The clamp of claim 5 wherein said connecting means comprises a projecting lug at said one end of said second clamp member, which fits within a slot at said adjacent end of said first clamp member, a bore extending through said lug and said adjacent end of said first clamp member, and a hinge pin received in said bore.

8. The clamp of claim 7 wherein said locking means comprises a latch hingedly connected to the other end of said first clamp member, a locking pin at the other end of said second clamp member, and a generally C-shaped portion at a free end of said latch for latching engagement with said locking pin.

9. The clamp of claim 8 wherein said handle attachment means includes a lug formed on said first clamp member intermediate the ends thereof, a bore extending through said last-mentioned lug, and a socket member having a yoke portion hingedly connected to said last-mentioned lug by a roll pin, said socket member also having an internally threaded socket portion for threaded reception therein of an externally threaded end of a handle member.

10. A clamp for a generally cylindrical container, comprising: a first clamp member having an arcuate inner surface; a second clamp member having an arcuate inner surface; means hingedly connecting the second clamp member at one end thereof to an adjacent end of said first clamp member, said connecting means including a projecting lug at said one end of said second clamp member, which fits within a slot at said adjacent end of said first clamp member, a bore extending through said lug and said adjacent end of said first clamp member, and a hinge pin received in said bore; means for locking the other end of said second clamp member to the other end of said first clamp member, said locking means including a latch hingedly connected to the other end of said first clamp member, a locking pin at the other end of said second clamp member, and a generally C-shaped portion at a free end of said latch for latching engagement with said locking pin; friction means lining said arcuate inner surface of said second clamp member; and handle attachment means hingedly connected to said first clamp member intermediate the ends thereof.

11. The clamp of claim 10 wherein said friction means is an elongated strip of resilient material adhered to said arcuate inner surface of said second clamp member and having a thickness at said arcuate inner surface of said second clamp member that is greater than the thickness at a radially innermost edge thereof.

12. The clamp of claim 10 including an undercut recess in the inner surface of said second clamp member, said friction means comprising an insert held in said recess and projecting radially inwardly of said inner surface of said second clamp member along the length thereof.

13. The clamp of claim 12 wherein said insert is an elongated strip of resilient material having a thickness within said recess greater than the thickness at a radially innermost edge thereof.

14. The clamp of claim 10 wherein said handle attachment means includes a lug formed on said first clamp member intermediate the ends thereof, a bore extending through said last-mentioned lug, and a socket member having a yoke portion hingedly connected to said last-mentioned lug by a roll pin, said socket member also having an internally threaded socket portion for threaded reception therein of an externally threaded end of a handle member.

* * * * *